United States Patent [19]

Allison et al.

[11] Patent Number: 4,777,965

[45] Date of Patent: Oct. 18, 1988

[54] DEVICE FOR MEASURING CERVICAL RANGE OF MOTION

[75] Inventors: John D. Allison, Shoreview; Marvin G. Lepley, South St. Paul; Corinne T. Ellingham, Edina; James F. Pohtilla, Plymouth, all of Minn.

[73] Assignee: Regents of the University of Minnesota, Minneapolis, Minn.

[21] Appl. No.: 802,179

[22] Filed: Nov. 26, 1985

[51] Int. Cl.$^4$ .............................................. A61B 5/10
[52] U.S. Cl. ..................................... 128/781; 128/782; 33/512
[58] Field of Search ..................... 128/774, 781–782; 33/511–512, 515, 381–382

[56] References Cited

U.S. PATENT DOCUMENTS

| | | | |
|---|---|---|---|
| 1,590,499 | 6/1926 | Cozad. | |
| 2,491,312 | 12/1949 | Henry et al. | 33/200 |
| 2,501,745 | 3/1950 | Sherman | 33/382 X |
| 2,565,381 | 8/1951 | Leighton | 33/221 |
| 2,677,894 | 5/1954 | Belgard | 33/200 |
| 3,429,052 | 2/1969 | Hembd et al. | 33/220 |
| 3,614,950 | 10/1971 | Rabey | 128/774 |
| 4,279,260 | 7/1981 | Stump | 128/774 |
| 4,328,620 | 5/1982 | Mack et al. | 33/174 |
| 4,444,204 | 4/1984 | Bryant et al. | 33/512 X |
| 4,485,825 | 12/1984 | Domjan et al. | 128/774 |
| 4,528,990 | 7/1985 | Knowles | 128/774 X |
| 4,586,515 | 5/1986 | Berger | 128/782 |

FOREIGN PATENT DOCUMENTS

| | | | |
|---|---|---|---|
| 3317918 | 6/1984 | Fed. Rep. of Germany | 128/774 |
| 1534545 | 7/1968 | France | 128/782 |

OTHER PUBLICATIONS

Catalog—Fred Sammons Inc., 1985 Professional Health Care Catalog.
"Neck Movements in Ankylosing Spondylitis and Their Responses to Physiotherapy"—Susan L. O'Driscoll, M.I.V. Jayson, H. Baddeley, Annals of the Rheumatic Diseases, 1979, vol. 37, pp. 64–66.
Brochure—"Myrin" Goniometer, LIC Rehab Care, Salna, Sweden.
"A New Neck Goniometer", N. Kadir, M. F. Grayson, A. A. J. Goldberg, Margaret C. Swain, Rheumatology and Rehabilitation, 1981, vol. 20, pp. 219–226.
"Report of Projects Completed May 1981-1983-"—Royal Ottawa Hospital, 1983.
"A Multiple Purpose Goniometer:, Marian Weiss, Archives of Physical Medicine & Rehabilitation, Apr. 1964, pp. 197, 198.
"An Experimental Study of Head Motion in Adult Males", Journal of the American Physical Therapy Association, Mar. 1964, vol. 44, No. 3, pp. 163–165.

Primary Examiner—Edward M. Coven
Assistant Examiner—Angela D. Sykes
Attorney, Agent, or Firm—Kinney & Lange

[57] ABSTRACT

A device and process for measuring cervical range of motion about three axes comprises an eyeglass frame which is supported on the nose and ears of a patient. A pendulum angle finder and a compass and the pendulum is mounted a horizontal axis and the compass needle is mounted about a vertical axis. The angle finder and compass are mounted on the eyeglass frame with a clamp that permits rotating the angle finder 90° to permit measuring angles about two mutually perpendicular axes in the horizontal plane to permit tri-planar angle measurements. The angle finder and compass can be adjusted to a zero position and cervical range of motion is then measured through the use of angle indictor scales provided on the angle finder and compass. Readings may be made about one, two, or all three axes of rotation.

8 Claims, 2 Drawing Sheets

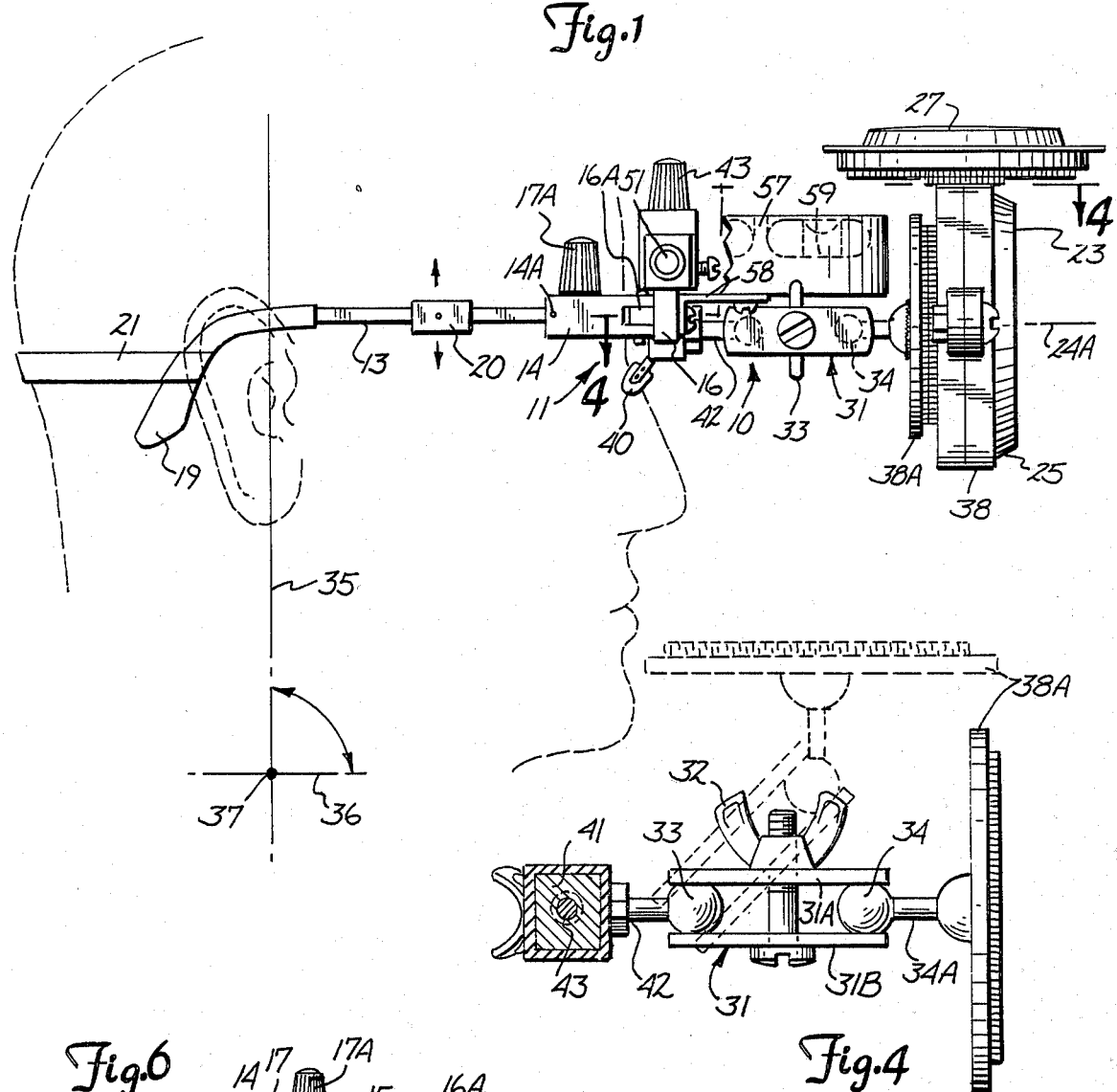
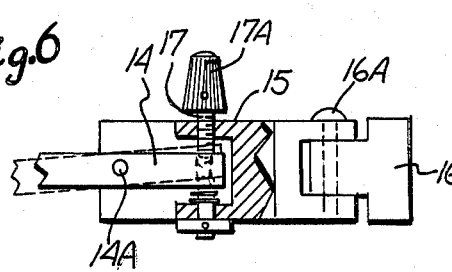
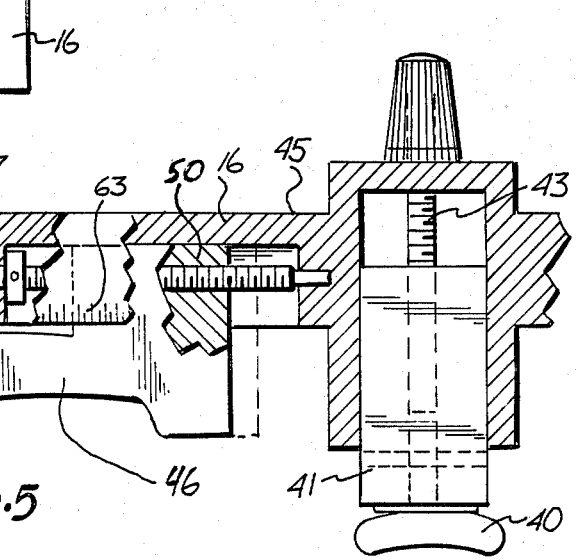

DEVICE FOR MEASURING CERVICAL RANGE OF MOTION

BACKGROUND OF THE INVENTION

This invention was made with Government support under Grant No. G008300075 awarded by the National Institute of Handicapped Research of the Department of Education. The Government has certain rights in this invention.

1. Field of the Invention

This invention relates to a device and related process for measuring the range of cervical motion of a patient about three axes of rotation.

2. Description of the Prior Art

Several devices have been used to measure the range of cervical motion. Typically, such devices have utilized an angle finder and/or compass detachably secured to the human body through the use of a belt or strap to obtain the necessary measurements.

U.S. Pat. No. 4,485,825 to Domjan et al discloses what is referred to as an arthrospinometer having an inclinometer and a north-south-seeking compass carried in a housing pivotally mounted on a base plate. The base plate has a scale thereon and an indicator is provided for indicating on the scale the degree of rotation relative to the base plate. There is also a scale for indicating the amount of rotation of the inclinometer and compass relative to the housing and this scale is rotatable relative to the housing about a common third axis. The base plate has a suction cup attached to its bottom side in order to secure the device to a portion of the human body. Such a method of securing the device to the human body does not facilitate the making of reproducible measurements as standardized placement and positioning are difficult.

The "Myrin" Goniometer produced by LIC Rehab Care utilizes an inclination needle and compass to indicate degree of rotation. The Myrin Goniometer is strapped to the body to take readings about a variety of joints. Reproducibility of data is very difficult as there are no established reference landmarks. Also, the Myrin Goniometer does not allow precise orientation of the inclination needle and compass as only the strap is used in mounting, making standardized measurements very difficult to reproduce for an objective comparison.

Other devices have been designed for measuring the range of cervical motion. In particular, U.S. Pat. No. 2,565,381 to Leighton discloses a device having a weighted pointer mounted within a housing having a rotatable calibrated dial. The device is attached to the body on one side of a joint and the weighted pointer is used to measure range of motion about the joint. U.S. Pat. No. 3,429,052 Hembd et al. discloses a similar device which is dampened to reduce the oscillation of the weighted pointer which occurs in the Leighton device. Neither of these devices permits the making of range of motion measurements in more than one plane without having to reattach the device at a new position on the body. In addition, the data obtained would likely not be reproducible as no predesignated landmarks are established.

Other methods used for obtaining range of motion measurements have used a more mechanical approach. For example, U.S. Pat. No. 1,590,499 to Cozad discloses a device which may be attached to a human arm across the elbow as the arm is flexed or extended. Range of motion measurements are taken through the use of a protractor mounted on the device and a pointer which moves relative to the movement of the arm. Devices of this type are difficult to use in obtaining objective range of cervical motion measurements. Also, such mechanical devices are not conducive to obtaining reproducible data concerning range of cervical motion.

Various devices have been mounted on eyeglass type frames in order to obtain vision related measurements. For example, U.S. Pat. Nos. 2,491,312 to Henry et al and 2,677,894 to Belgard disclose devices for taking ophthalmic measurements. The devices are designed to take measurements which facilitate the proper positioning of an eyeglass lens in front of the pupil. Such devices are of particular value to those patients wearing bifocal lenses. U.S. Pat. No. 4,328,620 to Mack et al. discloses a device which utilizes an eyeglass type frame to properly position an apparatus which registers the movements of the lower jaw with reference to the skull. The Mack device, however, is not capable of obtaining range of cervical motion measurements.

Cervical region pathology is a common problem in humans with the instance increasing with age. A major symptom or sign of pathology is loss of motion in one or more planes of movement and associated pain. Measurement of cervical motion of patients during the course of a therapeutic regimen provides objective data on the benefits of the selected treatment approach. Standardization of a protocol for measuring the motions of flexion/extension, lateral or side bending and with rotation is a prerequisite to satisfactory use of objective and comparative measurements of cervical range of motion, which in turn permits objective evaluation of the therapeutic regime.

SUMMARY OF THE INVENTION

The apparatus according to the present invention comprises a device to permit objectively measuring the range of cervical motion of a patient, particularly when the disclosed process is used. Objective and comparative measurements are taken by mounting the measurement device in a reference position using known reference points on the patient's head. Proper positioning is achieved according to the present invention in that an adjustable frame similar to an eyeglass frame is used to mount the motion measuring device to the patient's head. The frame is supported with a nose pad which when used with a pair of pivotally mounted temples or bows supported on the ears, provide repeatable reference positioning. The nose pad and temples are adjustable in order to permit the eyeglass frame to be properly leveled when positioned on the patient's head. The width of the eyeglass frame also may be adjusted to accommodate various size heads. The eyeglass frame has an adjustable strap which wraps around the back of the head in order to secure the eyeglass frame to the head following proper positioning. The bridge of the nose is a primary reference point which permits the frame to be quickly mounted and used.

Measurements of the range of cervical motion are obtained according to the invention through the use of a vertical angle measuring instrument (called angle finder) mounted on the frame and a compass secured to the top of the angle finder. An adjustable clamp is used to attach the angle measuring instrument and compass assembly to the eyeglass frame. The angle measuring instrument comprises a pendulum pivotally mounted on a horizontal axis relative to a vertical face that adjusts to gravitational change. The compass is a conventional magnetic needle compass. Lateral or side bending movement of the head and cervical spine are recorded with the angle finder in the coronal or frontal plane. The sagittal axis of the pendulum extends fore and aft in this position. The cervical spine and suboccipital flexion/extension measurements are read with the angle finder plane of movement in the sagittal plane (a vertical plane bisecting the body). The pendulum axis is oriented transversely (frontal or coronal axis) for these measurements. Rotational readings about a generally vertical axis are taken from the compass affixed to the angle finder.

BRIEF DESCRIPTION OF THE DRAWINGS

FIG. 1 is a side elevational view of a device for measuring cervical motion made according to the present invention, shown in place on a patient;

FIG. 4 is a fragmentary sectional view taken as on line 4—4 in FIG. 1;

FIG. 5 is a fragmentary front (anterior) elevational view of the frame used with the device of the present invention, with parts in section and parts broken away; and FIG. 6 is a fragmentary side (lateral) sectional view of a typical adjustable connector for the temple pieces to permit changing the relative angles of the frame.

DETAILED DESCRIPTION OF THE PREFERRED EMBODIMENTS

Figure 2:
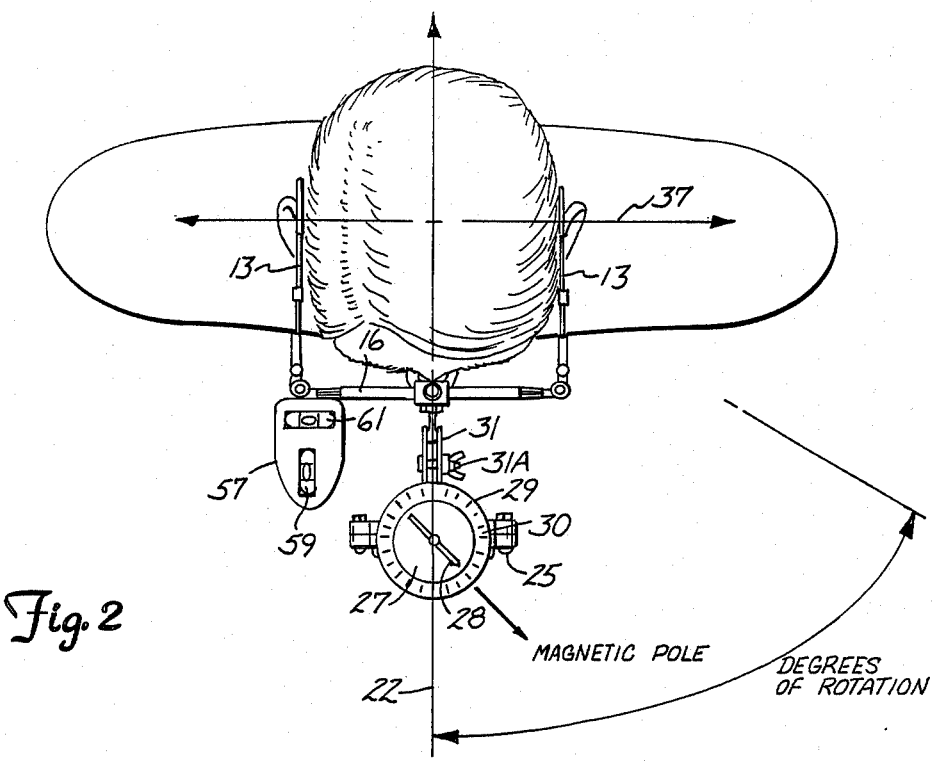
FIG. 2 is a top plan view of the device of FIG. 1.

A device for measuring range of cervical motion about three axes of rotation is generally indicated at 10 of FIG. 1. The range of motion measuring device includes an adjustable eyeglass frame 11 designed to be mounted to a human head. An angle finder and compass assembly 23 is attached to the eyeglass frame 11 with an adjustment clamp 31 (see also FIG. 4) that connects the assembly 23 to the eyeglass frame 11 in the center, between the eyes and for properly positioning the assembly 23 relative to the eyeglass frame 11.

The eyeglass frame 11 may be adjusted for sizing and proper positioning (leveling) of the angle finder and compass assembly 23 on the head. As shown perhaps best in FIG. 4 (and shown schematically because the adjustment is conventional), a pair of temples or bows 13 of the eyeglass frame 11 have first end portions 14 which are pivotally mounted about a horizontal axis on a pin 14A (see FIG. 4) in a temple connective piece 15. The connective piece 15 is attached to the front cross frame 16 with a normal hinge assembly 16A for folding the temples. The adjustable temples 13 may each be adjusted by turning screw 17 which rotates on the connective piece 15 and which is threaded through an opening in the end portion 14 to pivot the ear hook 19 and cause tilting of the front cross frame 16. The front cross frame is pivoted to a proper angle with respect to horizontal for establishing a standardized reference plane. Pivot control screws 17 have knobs 17A which operate the screws 17 which pivot the temples 13 on horizontal axis pins 14A. A second ear piece end 19 of each adjustable temple 13 is adapted to rest comfortably on the ear of the patient while simultaneously providing additional support to the apparatus. A strap 21 is provided to secure the apparatus to the head. The temples 13 can be lengthened or shortened by use of an adjustment clamp block 20 that permits two sections of the temple to slide longitudinally relative to each other as desired.

Figure 3:
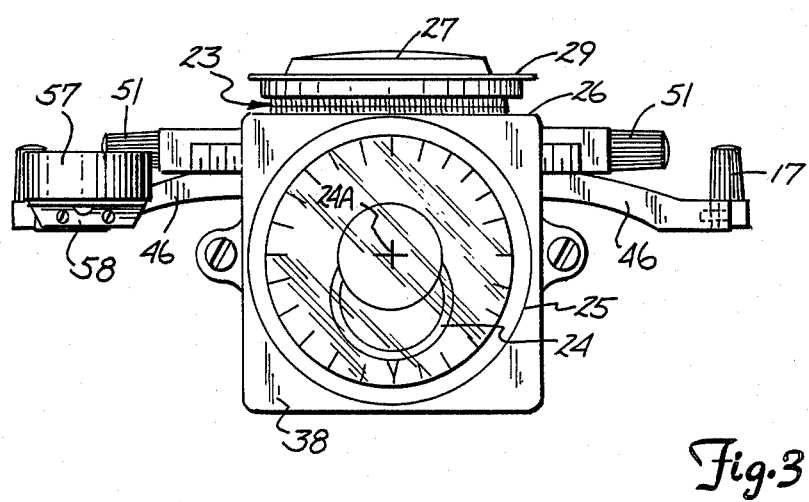
FIG. 3 is a front elevational view of the device of the present invention.

The angle finder and compass assembly 23 is connected to the eyeglass frame 11 through an adjustment clamp shown generally at 31. The clamp 31 is positioned above the patient's nose and thus centered on the head along the mid sagittal (bisecting fore and aft) plane 22 of the patient. The angle finder and compass assembly 23 comprises a pendulum angle measuring instrument, called an angle finder 25. The angle finder 25 has a pendulum 24 mounted to rotate about a first horizontal axis 24A (FIGS. 1 and 3) so the pendulum 24 seeks a vertical orientation. The angle finder measures angles relative to a vertical direction referenced to the face of the angle finder adjacent the pendulum. The pendulum has a pointer for ease of reference.

A compass 27 is attached by a suitable fastener such as a hook and loop fastener sold under the trademark Velcro to an upper edge 26 of the housing of angle finder 25. The compass 27 has a compass needle 28 rotatable about a second vertical axis perpendicular to the first horizontal axis and a rotatable outer rim 29 having a 360° scale 30 marked thereon. The rim can be rotated to place the zero scale mark in line with the needle 28. The compass 27 is mounted so that the pivot axis of the compass needle 28 is substantially perpendicular to the axis of the pendulum 24 of angle finder 25 and the needle axis will be vertical when the pendulum axis is horizontal. The angle finder and compass assembly 23, and its mounting clamp 31 permit effectively obtaining measurements of motion about three axes of cervical rotation.

The clamp 31 as shown is a universal clamp assembly having a tightening bolt and wing nut 32 that tightens a pair of plates 31A and 31B onto ball members 33 and 34. The adjustment clamp 31 is releasable to permit the angle finder and compass assembly 23 to be moved 90° from the position shown in FIG. 2. The 90° position (for measuring flexion/extension) is shown in FIG. 4 in dotted lines. Angle readings may be taken about any of the three axes of head movement or rotation. In the position shown in FIG. 2 movement (rotation) about the vertical axis 35 (FIG. 1) and horizontal fore and aft axis 36 (lateral bending axis) may be measured. The adjustment clamp 31 will permit the angle finder-compass assembly 23 to be pivoted about a vertical axis by loosening a wing nut and bolt 32. The adjustment clamp 31 permits the angle finder 25 to be rotated 90° from its first position, where the pendulum measures angles in the frontal plane as shown in FIG. 1 to a second position to measure bending in the sagittal plane (nodding). The angle finder 25 is used to measure lateral or side-to-side bending of the head in the frontal plane, that is, with the pendulum axis extending fore and aft, and it is used to measure flexion/extension of the cervical spine, i.e. "nodding" of the head, when in the sagittal plane, with the pendulum axis extending laterally and horizontally, that is, in direction parallel to the transverse axis 37 extending (ear-to-ear direction). The pendulum angle finder has a frame or housing 38 that houses the pendulum. A vertical face surface adjacent the pendulum has angle indicators so as the head moves the pendulum stays vertical and the amount of movement can be observed. The housing 38 is held onto a support plate 38A with hook and loop fasteners (sold under the trademark Velcro). The plate 38A has ball 34 mounted thereon through a shank 34A fixed to plate 38A.

A nose pad 40 is mounted on a slider block 41 housed in a sleeve 42 which is fixed to the front frame section 16. Ball 33 for clamp assembly 31 is fixed to sleeve 42. Vertical adjustment of the nose pad is accomplished by having a support screw 43 rotatably mounted in the center of the front frame section 16 and threaded into the slider block 41. The nose pad 40 provides support, and a point of reference for the apparatus. The eyeglass frame 11, and in particular front frame section 16, may be raised or lowered relative to the nose pad 40 to level the eyeglass frame prior to taking measurements. The front frame section 16 has a center portion 45 and laterally slideable side members 46 which are guided in receptacles formed in the front frame center portion 45. A separate screw 47 is mounted on each side of the center portion 45 and threads through a block 50 on the respective side members 46. Each screw 47 has a control knob 51 connected to it and when rotated, the width of the front frame section 16 can be adjusted to fit various size heads. The frame adjustments are conventionally done on ophthamalic instruments.

A level assembly 57 is attached to the eyeglass frame 11 with a bracket 58 that is fastened to the eyeglass frame with a screw. The level assembly 57 comprises two individual bubble levels, 59 and 61, oriented perpendicularly to one another and having their axes parallel. As shown, the bubble levels are coplaner. The level assembly 57 may be used so that the frame 11 is level and in a horizontal plane, through the use of adjustment screws 17 and 43 to indicate that the compass and angle indicator are referenced to a horizontal plane before movement.

A scale 63 is provided on the front frame section 16 of eyeglass frame 11 to indicate the position of side portion 46 of the frame when they are fitted. The width can be recorded for a patient to aid in adjusting the frame width during subsequent cervical range of motion measurements of the same patient.

The support frame is quickly mounted on the patient's head using the nose pad 40 and temples 13. Precise leveling is permitted by adjusting the elevation of the frame 11 relative to the nose pad 40 through the use of vertical adjustment screw 43, and the size of the frame can be changed by adjusting the width of the front frame section 16 through the use of lateral adjustment screws 47. The angle of temples 13 relative to the front frame section 16 can be adjusted through the use of pivot control knobs 17A and their associated screws 17. Precise leveling is indicated by the level assembly 57.

The eyeglass frame 11 is supported on the bridge of the nose through the use of nose pad 40 and on the ears through the use of ear hooks 19. The apparatus is retained on the patient's head by the strap 21. The proper reference landmarks (nose and ears) quickly and easily locate the frame at a repeatable position. Adjustment clamp 31 is used to properly orient the angle finder and compass assembly 23 so the angle finder pendulum indicates zero and the compass needle is free to rotate. The rotatable rim 29 of the compass is then rotated such that a zero position is established according to the initial direction of the compass needle.

Readings then may be taken about axes of rotation of the cervical spine using the compass 27 and angle finder 25. Rotational readings about a vertical axis are taken from the compass scale 30. Cervical spine and suboccipital flexion/extension (nodding) measurements are read with the angle finder pendulum axis perpendicular to the sagittal plane. Once these readings are taken, lateral or side-to-side bending movement of the head and cervical spine may be recorded after the angle finder 25 has been rotated 90° by loosening adjustment clamp 31 to place the angle finder such that it will indicate movement in the coronal or frontal plane.

Care is taken in making all of the measurements to assure that cervical spine rotation occurs about the proper axes through the use of bubble levels 59 and 61 mounted on level assembly 57. The head of the patient can be returned to the reference plane between readings. Initial readings are used as references for future readings to detect improvement or regression due to treatment.

The compass 23 is a magnetic type angle determining means or angle finder, as well, and the pendulum angle finder 25 is a gravity type angle finder or angle determining means. These angle finders also may be termed angle meters.

Although the present invention has been described with reference to preferred embodiments, workers skilled in the art will recognize that changes may be made in form and detail without departing from the spirit and scope of the invention.

What is claimed is:

1. An apparatus for measuring the range of cervical motion about at least two axes of rotation including:
   a frame for detachably mounting the apparatus to a human head, said frame having a nose pad adapted to be supported on the bridge of the nose as a reference location, and temple pieces adapted to be positioned on opposite side of a head for supporting and stabilizing the frame on the ears of a wearer; and
   a first vertical angle finder means and second angle determining means both coupled to the frame for determination of angle with respect to reference locations, respectively, using portions of the first and second means mounted on the wearer of the frame only, the angle finder means detecting rotations about a first axis and the second means detecting rotations about a second axis substantially perpendicular to the first axis.

2. The apparatus according to claim 1 and means for adjustably mounting the angle finder and second angle determining means to the frame, said means for adjustably mounting permitting adjusting the position of the angle finder and second means substantially 90°.

3. The apparatus according to claim 1 wherein said frame includes means to pivotally mount the temple pieces to other portions of the frame about a horizontal axis and screw adjustment means to permit tilting the frame about a horizontal axis relative to the temple pieces.

4. The apparatus according to claim 1 wherein said angle finder comprises a pendulum mounted about the first axis, said first axis being substantially horizontal in use.

5. The apparatus of claim 4 wherein the second angle determining means comprises a compass needle pivotally mounted on an axis substantially perpendicular to the first axis.

6. The apparatus according to claim 5 wherein said compass has a rotatable face for zeroing the reading and has an angular scale marked thereon.

7. The apparatus according to claim 1 and a level assembly attached to said frame comprising two bubble levels oriented perpendicularly to one another and having axes defining a plane.

8. A process for measuring cervical range of motion comprising the steps of:
 a. mounting an a frame having a front cross frame, a nose piece and hinged temple pieces supportable on a human head;
 b. providing a level assembly having two mutually perpendicular bubble levels mounted thereon to indicate level condition in two axes of a plane;
 c. providing a compass and an angle indicator for vertical angles on the frame and oriented to indicate angles about substantially vertical and horizontal axes, respectively; and
 d. rotating the head about vertical and horizontal axes and taking measurements with the compass and angle finder to determine the range of motion about said axes.

* * * * *